United States Patent [19]

Katzman

[11] Patent Number: 6,067,989
[45] Date of Patent: *May 30, 2000

[54] **BREATH TEST FOR THE DIAGNOSIS OF *HELICOBACTER PYLORI* INFECTION IN THE GASTROINTESTINAL TRACT**

[75] Inventor: Daniel E. Katzman, Jerusalem, Israel

[73] Assignee: Oridion Medical, Ltd., Jerusalem, Israel

[*] Notice: This patent issued on a continued prosecution application filed under 37 CFR 1.53(d), and is subject to the twenty year patent term provisions of 35 U.S.C. 154(a)(2).

[21] Appl. No.: 08/805,415

[22] Filed: Feb. 26, 1997

[51] Int. Cl.⁷ .............................. A61B 19/00; C07C 2/02
[52] U.S. Cl. ........................... 128/898; 600/532; 422/84; 73/23.3
[58] Field of Search .............................. 128/898; 60/529, 60/532; 422/84; 73/23.3

[56] References Cited

U.S. PATENT DOCUMENTS

| | | | |
|---|---|---|---|
| 4,440,177 | 4/1984 | Anderson et al. | 128/719 |
| 4,444,201 | 4/1984 | Itoh | 128/716 |
| 4,830,010 | 5/1989 | Marshall | 128/630 |
| 4,947,861 | 8/1990 | Hamilton | 128/719 |
| 5,042,501 | 8/1991 | Kenny et al. | 128/719 |
| 5,046,017 | 9/1991 | Flewelling et al. | 364/497 |
| 5,063,275 | 11/1991 | Rosenfeld et al. | 250/343 |
| 5,231,591 | 7/1993 | Flewelling et al. | 364/497 |
| 5,309,921 | 5/1994 | Kisner et al. | 128/719 |
| 5,363,857 | 11/1994 | Howard | 128/718 |
| 5,510,269 | 4/1996 | Black et al. | 436/164 |
| 5,543,521 | 8/1996 | Chan et al. | 544/349 |
| 5,570,697 | 11/1996 | Walker et al. | 128/719 |
| 5,640,014 | 6/1997 | Sauke et al. | 250/339.03 |
| 5,705,735 | 1/1998 | Acorn | 73/23.3 |
| 5,719,052 | 2/1998 | Ito et al. | 435/287.1 |
| 5,848,975 | 12/1998 | Phillips | 600/532 |
| 5,944,670 | 8/1999 | Katzman | 600/543 |
| 5,957,858 | 9/1999 | Micheels et al. | 600/529 |
| 5,962,335 | 10/1999 | Katzman | 436/181 |
| 5,964,712 | 10/1999 | Kubo et al. | 600/529 |

FOREIGN PATENT DOCUMENTS

| | | | |
|---|---|---|---|
| 0 204 438 | 12/1986 | European Pat. Off. | C12Q 1/58 |
| 0 206 625 | 12/1986 | European Pat. Off. | A61K 33/00 |
| WO 95/11672 | 5/1995 | WIPO | A61K 9/28 |

OTHER PUBLICATIONS

Bloch, K., *The Journal of Biological Chemistry*, "The Metabolism of I(+)–Arginine in the Rat", vol. 165, No. 2, pp. 469–484, 1946.

Caldwell, S.H., et al. *Clinical Research*, "How Common is *Campylobacter Pylori* in Persons without Dyspepsia?", vol. 37, No. 1, 1989.

Caldwell, S.H., et al. *The American Journal of Medicine*, "Possible Role of *Campylobacter Pylori* in Idiopathic Hyperammonemia", vol. 87, pp. 249–250, 1989.

DeCross, A.J., et al. *Journal of Clinical Microbiology*, "Metronidazole Susceptibility Testing for *Helicobacter pylori* Comparison of Disk, Broth, and Agar Dilution Methods and Their Clinical Relevance", vol. 31, No. 8, pp. 1971–1974, 1993.

Dye, K.R., et al. *Digestive Diseases and Sciences*, "Ultrastructure of Another Spiral Organism Associated with Human Gastritis", vol. 34, No. 11, pp. 1787–1791, 1989.

Evans, D.J., *Gastroenterology*, "A Sensitive and Specific Serologic Test for Detection of *Campylobacter pylori* Infection", vol. 96, No. 4, pp. 1004–1008, 1989.

Frierson, H.F. Jr., et al. *Laboratory Investigation*, "A Spiral Bacterium Distinct from *Campylobacter Pylori* that Causes Gastritis in Humans", vol. 60, No. 1, 1989.

Godle, H., et al. *Nuclear Science Abstracts*, vol. 4, No. 18, p. 806, 1950.

Graham, D.Y., et al. *The American Journal of Gastroenterology*, "*Campylobacter pyloridis* Gastritis: The Past, the Present, and Speculations about the Future", vol. 82, No. 4, pp. 283–286, 1987.

Graham, D.Y., et al. *The Lancet*, "*Campylobacter Pylori* Detected Noninvasively by the [$^{13}$C]–Urea Breath Test", vol. I, pp. 1174–1177, 1987.

Graham, D.Y., et al. *Scandinavian Journal of Gastroenterology*, "Epidemiology of *Campylobacter pylori* Infection: Ethnic Considerations", pp. 9–13, 1988.

Graham, D.Y., et al. *The Journal of Infectious Diseases*, "Effect of Age on the Frequency of Active *Campylobacter pylori* Infection Diagnosed by the $^{13}$C–Urea Breath Test in Normal Subjects and Patients with Peptic Ulcer Disease", vol. 157, No. 4, pp. 777–780, 1988.

Graham, D.Y., et al. *The American Journal of Gastroenterology*, "In Vivo Susceptibility of *Campylobacter pylori*", vol. 84, No. 3, pp. 233–238, 1989.

Kerr, D., et al. *The Lancet*, "Adrenaline Response to Hypoglycemia and Insulin Species", vol. I, p. 836, 1989.

Klein, P.D., *Stable Isotopes in Nutrition Research*, "Clinical Applications of $^{13}CO_2$ Measurements" pp. 2698–2701, 1982.

(List continued on next page.)

Primary Examiner—John G. Weiss
Assistant Examiner—Joseph F. Weiss, Jr.
Attorney, Agent, or Firm—Fish & Neave; Jeffrey H. Ingerman; Joel Weiss

[57] ABSTRACT

A breath test for diagnosing the presence of *Helicobacter pylori* in a subject is described. The method of diagnosing *Helicobacter pylori* is performed as follows. First, a safe and effective amount of urea, preferably appropriately labelled, is administered to the subject. Second, a plurality of the exhaled breaths of the subject is analyzed to detect the concentration of a cleavage product or products, produced when urease cleaves the substrate. The measured concentrations are then fitted to a curve, and the derivative is then calculated, to indicate the presence or absence of *Helicobacter pylori* infection in the subject.

10 Claims, No Drawings

OTHER PUBLICATIONS

Klein, P.D., *The Lancet,* "Water Source as Risk Factor for *Helicobacter pylori* Infection in Peruvian Children" vol. 337, No. 8756, pp. 1503–1506, 1991.

Klein, P.D., et al. *The American Journal of Gastroenterology,* "Noninvasive Detection of *Helicobacter pylori* Infection in Clinical Practice: The $^{13}$C Urea Breath Test", vol. 91, No. 4, pp. 690–694, 1996.

Kornberg, H.L., Davies, R.E., *II$^e$ Congres International de Biochimie,* "The Metabolism of Urea in the Cat", 1959.

Langham, W.H., *The Journal of Biological Chemistry,* "Studies on the Metabolism of Radioactive Nicotinic Acid and Nicotinamide in Mice", vol. 176, No. 1, pp. 249–257, 1948.

Leifer, E., et al. *Science,* "Metabolism of $C^{14}$–labeled Urea", vol. 108, p. 748, 1948.

Marshall, B.J., et al. *The Lancet,* "Unidentified Curved Bacilli in the Stomach of Patients with Gastritis and Peptic Ulceration", vol. I, pp. 1311–1315, 1984.

Marshall, B.J., et al. *The Medical Journal of Australia,* "Pyloric Campylobacter Infection and Gastroduodenal Disease", vol. 142, pp. 439–444, 1985.

Marshall, B.J., *The Journal of Infectious Diseases,* "*Campylobacter pyloridis* and Gastritis", vol. 153, No. 4, pp. 650–657, 1986.

Marshall, B.J., et al. *The Journal of Nuclear Medicine,* "Sensitive, Specificity and Reproducibility of the C–14 Urea Breath Test: Evaluation in Patients with *C. pylori*", vol. 29, No. 5, p. 790, 1988.

Marshall, B.J., *The American Journal of Gastroenterology,* "Should We Now, Routinely, Be Examining Gastric Biopsies for *Campylobacter pylori?*", vol. 83, No. 5, pp. 479–481, 1988.

Marshall, B.J., *Gastroenterologie Clinique et Biologique,* "Experimental models in vivo for *Campylobacter pylori*", vol. 13, 1989.

Marshall, B.J., et al. *Gastroenterology,* "Microdose, Capsule–Bases, 14C–Urea Breath Test For *H. Pylori*", vol. 96, No. 5, p. 321, 1989.

Marshall, B.J., et al. *Gastroenterology,* "Urea Protect *Helicobacter (Campylobacter) pylori* from the Bactericidal Effect of Acid", vol. 99, No. 3, 1990.

Marshall, B.J., et al. *Gastroenterology,* "Gastric Suction Biopsy—A Non–endoscopic Method to Diabnose *Helicobacter Pylori*", vol. 98, No. 5, p. 83, 1990.

Marshall., B.J., *The American Journal of Gastroenterology,* "*Helicobacter pylori*", vol. 89, No. 8, pp. 116–128, 1994.

Opekun, A.R., et al. *Digestive Diseases and Sciences,* "[$^{13}$C] Aminopyrine Breath Test Detects Altered Liver Metabolism Caused by Low–Dose Oral Contraceptives", vol. 40, No. 11, pp. 2417–2422, 1995.

Warren, J.R., *The Lancet,* "Unidentified Curved Bacilli on Gastric Epithelium in Active Chronic Gastritis", pp. 1273–1275, 1983.

Watkins, J.B., *The Journal of Laboratory and Clinical Medicine,* "$^{13}$C–trioctanoin: a Nonradioactive Breath Test to Detect Fat Malabsorption" vol. 90, No. 3, pp. 422–430, 1977.

Marshall, B.J., *The American Journal of Gastroenterology,* "Rapid Urease Test in the Management of *Campylobacter pyloridis*–Associated Gastritis", vol. 82, pp. 200–210, 1987.

Marshall, B. J., *Gastroenterology,* vol. 92, p. 1517, 1987

Marshall, B.J., Gastroenterology, "Fifteen Minute Urea–C14 Breath Test for the Diagnosis of Campylobacter Associated Gastritis", vol. 92, p. 1517, 1987.

Marshall, B.J., et al., *The Journal Of Nuclear Medicine,* "Carbon–14 Urea Breath Test for the Diagnosis of *Campylobacter pylori* Associated Gastritis", vol. 29, pp. 11–16, 1988.

Marshall, B.J., *Clinical Research,* "A Rapid 14C–Urea Breath Test for the Diagnosis of *C. pylori* Associated Gastritis", vol. 36, p. 14A, 1988.

Marshall, B.J., *The American Journal of Gastroenterology,* "Is CLOtest Alone Adequate to Diagnose *Campylobacter–pylori?*", vol. 83, No. 9 p. A284, 1988.

Dye, K.R., et al., *Gastroenterology,* "Comparison of Carbon–14 Urea Breath Test Microbiology and Histology for the Diagnosis of *Campylobacter–pylori*", vol. 83, No. 9 p. 1032. 1988.

Marshall, B.J., *Jama–Journal Of The American Medical Association,* "*Campylobacter–pylori*—Diagnosis and Treatment", p. 2916, 1988.

Marshall, B.J., *Scandinavian Journal Of Gastroenterology,* "The *Campylobacter pylori* Story", vol. 23, pp. 58–66, 1988.

Caldwell, S.H., et al., *Drug Therapy,* "*Campylobacter pylori* and Peptic Disease," pp. 92–106, 1989.

Marshall, B. J., *Supplement To Gastroenterology,* "Simplifying the Urea Breath Test for *C.pylori*", vol. 96, p. A321, 1989.

Marshall, B. J., *The Medical Journal Of Australia,* "*Campylobacter pylori* Infection: Diagnosis and Therapy", vol. 151, No. 7, pp. 426–427, 1989.

Marshall, B. J., *Supplement to Gastroenterology,* "$^{14}$C–Urea Breath Test for *H. pylori*", vol. 99, No. 3, pp. 698–702, 1990.

Marshall, B. J., *The American Journal of Gastroenterology,* "A 20–Minute Breath Test for *Helicobacter pylori*", vol. 86, No. 4, pp. 438–445, 1991.

Press, W.H., et al., *Numerical Recipes in C,* 2nd Ed., pp. 186–189, 661–666, 671–681, Cambridge Univ. Press, New York, 1992.

Marshall, B. J., *Gastroenterologist,* "*Helicobacter pylori*: A Primer for 1994", vol. 1, No. 4, pp. 241–247, 1993.

Stubbs, J.B., et al. *JNM,* "Radiation Dose Estimates for the Carbon–14–Labeled Urea Breath Test", vol. 34, No. 5, pp. 821–825, 1993.

Klein, P.D., et al., *The American Journal of Gastroenterology,* "Minimum Analysis Requirements for the Detection of *Helicobacter pylori* Infection by the $^{13}$C–Urea Breath Test", vol. 88, pp. 1865–1869, 1993.

*NIH Consensus Statement,* 12:1–23, 1994.

Barrett, L.J., et al. *ASM Las Vegas 1994,* "Evaluation of Pyloriscreen Assay for Detection of *H. pylori* Infection vs. Culture, Histology CLOtest and $^{14}$C Urea Breath Test", p. 296, 1994.

Combs, M.J., et al. *JNM,* "Dosimetry and Reproducibility of a Capsule–Based C–14 Urea Breath Test", vol. 36, No. 5, p. 98P, 1995.

Cutler, A.F., et al., *Gastroenterology,* "Accuracy of Invasive and Noninvasive Tests to Diagnose *Helicobacter pylori* Infection", 109:136–141, 1995.

Koletzko, S., et al., *The Lancet,* "Isotope–selective Non–dispersive Infrared Spectometry for Detection of *Helicobacter pylori* Infection with $^{13}$C–urea Breath Test", 345:961–2, 1995.

Combs, M.J., et al. *Gastroenterology*, "Safety and Reproducibility of the 14C–Urea Breath Test", vol. 108, No. 4, p. A74, 1995.

Bielanski, W., et al., *Journal of Physiology And Pharmacology*, "Microdose of $^{14}$C–Urea Breath Test in Detection of *Helicobacter pylori*", vol. 47, No. 1, pp. 91–100, 1996.

Sue, M., *Gastroenterology*, Comparison of Two Treatment Strategies for the Eradication of *H. pylori* Utilizing a Screening Antibody Serum Blot Test and Confirmatory C–14 Breath Test, vol. 110, No. 4, p. A266, 1996.

Peura, D.A. et al., *American Journal of Gastroenterology*, "Microdose $^{14}$C–Urea Breath Test Offers Diagnoses of *Helicobacter pylori* in 10 Minutes", 91:233–238, 1996.

World Health Organization, *World Health Report 1996*, p. 59, 1996.

Marshall, B. J., *Chang Gung Medical Journal*, vol. 20, No. (2), (Supp. 1) p. 8, 1997.

BREATH TEST FOR THE DIAGNOSIS OF *HELICOBACTER PYLORI* INFECTION IN THE GASTROINTESTINAL TRACT

FIELD AND BACKGROUND OF THE INVENTION

The present invention relates to a breath test for the diagnosis of *Helicobacter pylori* infection in the gastrointestinal tract and, more particularly, to a breath test which is rapid and convenient.

Gastrointestinal infections caused by *Helicobacter pylori* result in a variety of disorders, such as duodenal and gastric (stomach) ulcers [*NIH Consensus Statement*, 12:1–23, 1994]. Furthermore, these infections have been implicated in stomach cancer [The World Health Organization's *World Health Report*, 1996]. Clearly, rapid, accurate and non-invasive methods of detection of *Helicobacter pylori* are necessary.

A number of methods for such detection are currently available. For example, endoscopy of the stomach can be performed in order to obtain a tissue biopsy [Cutler, A. F. et al., *Gastroenterology*, 109:136–141, 1995]. The biopsy can then be examined by a number of methods, including microscopy and histological methods. Unfortunately, this procedure has a number of drawbacks. First, it is highly invasive. Second, the patient must be sedated during the procedure. Third, the test cannot measure *Helicobacter pylori* activity in "real time". That is, there is a significant delay between the time the *Helicobacter pylori* activity takes place, and the time such activity is measured by the test.

Another, somewhat less invasive test is a blood test. A sample of blood is withdrawn and tested for the presence of antibodies to *Helicobacter pylori*. This test also has a number of drawbacks. Like the biopsy test, the blood test cannot directly measure *Helicobacter pylori* activity, particularly since antibodies can remain in the body for 6–24 months after an infection has been eradicated. Thus, slick a test measures previous exposure to *Helicobacter pylori* and not necessarily a current infection. A far less invasive method is a breath test. As described in U.S. Pat. No. 4,830,010 to Marshall (hereinafter referred to as "Marshall"), this method involves orally administering isotopically-labelled urea to a subject and then analyzing exhaled breath of the subject for the presence of isotopically-labelled carbon dioxide or ammonia, which indicates the presence of an infection in the gastrointestinal tract. *Helicobacter pylori* produces a large quantity of the enzyme urease, which hydrolyzes urea to form carbon dioxide and ammonia. At least one isotopically-labelled product is then exhaled by the subject and can be detected in the exhaled breath of the subject by an appropriate measuring instrument. Thus, the breath test for diagnosing *Helicobacter pylori* is relatively non-invasive.

Unfortunately, this test is not sufficiently rapid to permit immediate measurement of *Helicobacter pylori* activity. For example, in the Marshall disclosure, the breath of the subject is collected twenty minutes after administration of the substrate, by bubbling through a scintillation solution. The solution is then placed in a scintillation counter, which is presumably not located at the physician's office. Thus, the subject must wait about twenty minutes to give the sample, and must then wait for the laboratory to return the results. Clearly, this method cannot be used to analyze and immediately give the results of the test, within the context of a single visit to the office of the physician, for example.

This basic urea breath test for the diagnosis of *Helicobacter pylori* infection in the gastrointestinal tract as been examined in the clinical literature. Again the results of the test cannot be provided immediately. For example, Koletzko and co-workers describe the analysis of such a urea breath test with an isotope-selective non-dispersive infrared spectrometer [Koletzko et al., *Lancet*, 345:961–2, 1995]. liven using such a sophisticated instrument, the subjects were still required to wait 15 and 30 minutes before breath samples were taken. Clearly, such a long delay to obtain breath samples, as well as the long wait between samples, is both inconvenient and potentially reduces patient compliance. The potential reduction in patient compliance can have serious consequences, since as noted above, *Helicobacter pylori* has been implicated in stomach cancer as well as ulcers.

Furthermore, the sample or samples are collected from the patient and then sent to a laboratory for analysis, causing a delay in the determination of the results and forcing the subject to return to the office of the physician in order to obtain the results. If the test does not yield meaningful results, the entire process must be repeated again. The requirement for multiple office visits also potentially reduces patient compliance.

The most rapid breath test currently proposed, the "Pytest" from Tri-Med Specialties, Charlottesvilee, N.C., USA, takes about 10–15 minutes to perform but uses carbon-14 isotopically-labelled urea, which is radioactive [Peura, D. A. et al., *Am. J. Gastro.*, 91:233–238, 1996]. Thus, this test has all the disadvantages of radioactivity. Not only is radioactivity potentially hazardous, but it restricts the test to large testing centers which can handle such materials. Thus, the test could not be performed in the office of the average physician, so that multiple office visits are again required.

In both cases the patient must wait at least 10–15 minutes before the sample is collected partly because only one sample is taken. Thus, in order for the test to have sufficient sensitivity, the level of isotopically-labelled carbon dioxide must be relatively high. However, such a single point determination potentially decreases the accuracy of the test, as well as increasing the risk of ambiguous results.

A better breath test would involve the collection of multiple samples, yet would be sufficiently rapid to permit both the samples to be obtained and the results to be determined within a short period of time, for example about 15 minutes. Such a test should also be sufficiently simple for a physician, such as a gastroenterologist, to perform in the office, without the need for a special testing center or laboratory.

There is thus a widely recognized need for, and it would be highly advantageous to have, a breath test for the detection of *Helicobacter pylori* infection of the gastrointestinal tract in a subject, which is extremely rapid and which can provide results with relatively little delay, for example in the context of a single visit to a physician's office.

SUMMARY OF THE INVENTION

According to the present invention there is provided a method for the diagnosis of *Helicobacter pylori* in gastrointestinal tract of a subject, including the steps of: (a) administering urea to the subject, said urea being cleavable by urease to form a cleavage product; (b) analyzing a plurality of exhaled breaths of the subject for a concentration of said cleavage product, said concentration indicating activity of *Helicobacter pylori* in the gastrointestinal tract of the subject; (c) fitting said concentrations to a curve; and (d) analyzing curve by derivativation.

Preferably, the step of analyzing said exhaled breath of the subject is repeated substantially until a particular time period has elapsed. Alternatively and preferably, the step of analyzing said exhaled breath of the subject is repeated substantially until a particular accuracy for analyzing said curve is reached. Also preferably, the breath of the subject is analyzed by an infrared spectrometer.

According to further preferred embodiments of the present invention, the urea is isotopically-labelled. The cleavage product is preferably carbon dioxide, and the carbon dioxide is carbon-13 isotopically-labelled. Alternatively and preferably, the cleavage product is ammonia, and the ammonia is nitrogen-15 isotopically-labelled.

DESCRIPTION OF THE PREFERRED EMBODIMENTS

The present invention is of a breath test which can be used to detect the presence of *Helicobacter pylori* species in the gastrointestinal tract of a subject. Specifically, the present invention can be used to diagnose the presence of *Helicobacter pylori* by orally administering a safe and effective amount of urea to a subject and then detecting the concentration of one of the cleavage products of urea, carbon dioxide or ammonia, or both cleavage products, in the exhaled breath of the subject, after a suitable time period has elapsed, preferably about eight minutes after the oral administration of urea. A curve is fitted to these measured concentrations and is then analyzed, preferably by determining the rate of rise of the curve. Such an analysis indicates the level of activity of *Helicobacter pylori* species in the subject, which can be used to diagnose the presence of *Helicobacter pylori* in the gastrointestinal tract of the subject. Hereinafter, the term "cleavage product of urea" refers to carbon dioxide and ammonia.

Preferably at least a majority of the exhaled breaths, and most preferably every exhaled breath, is sampled for a given time period or until the determination of the level of *Helicobacter pylori* activity has reached a preset accuracy.

By "cleaves" it is meant that the enzyme can break at least one chemical bond of urea, forming a plurality of products, by a chemical process including, but not limited to, hydrolysis. A product so formed is a "cleavage product". The concentration of the cleavage product or products indicates the level of activity of the *Helicobacter pylori* species in the gastrointestinal tract of the subject, which can be used to determine a diagnosis of infection by a *Helicobacter pylori* species. A positive diagnosis indicates that *Helicobacter pylori* is present in the gastrointestinal tract of the subject. Such a method for diagnosis call also be referred to as a "breath test".

Hereinafter, the term "subject" refers to a human or lower animal on whom the method of diagnosing *Helicobacter pylori* infection of the gastrointestinal tract is performed.

The term "safe and effective amount of substrate" refers to an amount of a substrate which is sufficient to produce a detectable level of a cleavage product or products, without an untoward level of adverse side effects, such as toxicity, irritation, allergy or hypersensitivity responses. The level of any such side effects should be commensurate with acceptable risk/benefit ratios.

Examples of appropriate labels for the substrate, and hence for the cleavage product or products, are those which can be detected by an appropriate measuring instrument, but which are substantially not harmful or toxic to the subject including, but not limited to, carbon-13 or carbon-14, oxygen-18 or nitrogen-15, isotope-labelling. An isotope is a form of an element, such as carbon, with a specific mass. For example, carbon-12 has a mass of 12 atomic mass units. The term "isotope-labelling" means that the naturally more abundant isotope of each of these elements is at least partially replaced by a less abundant isotope. For example, the naturally more abundant carbon-12 atoms could be at least partially replaced by the less abundant carbon-13 atoms, permitting the cleavage product or products which carry the label to be more easily detected, since the less abundant isotope can be distinguished from the naturally more abundant isotope. Furthermore, the advantage of certain isotopes such as carbon-13 is that they are stable, so that they are not radioactive, unlike isotopes such as carbon-14. Therefore, preferably stable, non-radioactive isotopes such as carbon-13 are used as labels.

Compositions for oral administration include powders or granules, suspensions or solutions in water or non-aqueous media, sachets, capsules or tablets. Thickeners, diluents, flavorings, dispersing aids, emulsifiers or binders may be desirable.

Following the step of orally administering the urea to the subject, the exhaled breath of the subject is analyzed to detect a cleavage product or products, which indicate the presence of *Helicobacter pylori* in the gastrointestinal tract of the subject. The product or products are detected by analyzing a gas sample of the exhaled breath of the subject with a measuring instrument. Such a gas sample can be obtained in a number of ways including, but not limited to, having the subject exhale or blow into a tube connected to the measuring instrument. Preferably, a nasal cannula is used. Such a cannula includes a section of tubing, usually plastic, with two prongs. Each prong is inserted into a nostril and the cannula is then connected to the measuring instrument. As the patient exhales through the nose, the exhaled air flows through the cannula to the measuring instrument.

The type of measuring instrument used to detect the product or products depends upon the type of label. For example, if a carbon-13 isotopically-labelled substrate is used, the carbon-13 isotopically-labelled cleavage product or products can be detected by using a measuring instrument including, but not limited to a mass spectrometer or a gas analyzer, which is sensitive to the carbon-13 isotope. The ratio of the concentration of carbon-13 isotopically-labelled cleavage product or products to the concentration of carbon-12 cleavage product or products is then determined. Since carbon-12 is the more abundant isotope in nature, carbon-12 atoms are more abundant in unlabelled molecules. Thus, a higher carbon-13/carbon-12 ratio indicates a higher concentration of the carbon-13 isotopically-labelled cleavage product or products, which positively indicates the presence of *Helicobactier pylori* in the gastrointestinal tract of the subject.

Preferably, at least one of the cleavage products is carbon-13 isotopically-labelled carbon dioxide. Examples of measuring instruments which can be used with carbon-13 isotopically-labelled carbon dioxide include, but are not limited to, an infrared spectrometer. These infrared spectrometers are well known in the art, and have the advantage of being both rapid and accurate, as well as sensitive. Examples of such infrared spectrometers are disclosed in U.S. Pat. No. 5,063,275, herein incorporated by reference.

Alternatively and preferably, at least one of the cleavage products is nitrogen-15 isotopically-labelled ammonia. Of course, both carbon-13 isotopically-labelled carbon dioxide and nitrogen-15 isotopically-labelled ammonia could be present, providing that the substrate has both labels. Both ammonia and carbon dioxide have the advantage of being molecules which are present in the exhaled breath of the subject.

In any case, the measuring instrument used to detect the cleavage product or products must have a number of characteristics. The measuring instrument must be able to measure the concentration of the product or products extremely rapidly. Furthermore, either the measuring instrument itself, or an associated device, must be able to perform the associated analysis, including both the fitting of the curve and the analysis of the curve. Such analyses must be performed rapidly. Preferably, the measuring instrument, alone or in conjunction with the associated device, should be able to measure the concentration and perform the associated analysis within about 10 seconds, and most preferably within about 3 seconds, particularly if substantially every exhaled breath of the subject is to be analyzed.

The term "suitable time period" refers to the length of time required for a cleavage product or products to form and to be exhaled in the breath of the subject. Thus, a number of events must occur. First, the administered urea must be accessible to Helicobacter pylori, or a part thereof such as urease. Then, the administered urea must be cleaved by urease of Helicobacter pylori to form a cleavage product or products. The cleavage product or products must be absorbed into the blood and then pass into the lungs. Next, the cleavage product or products must be exhaled in the breath of the subject. Finally, the presence of the cleavage product or products must be detected in the exhaled breath.

Furthermore, the "suitable time period" should be such that the curve of measured concentrations of cleavage product or products in the exhaled breath of the subject is substantially linear. Generally, the concentration will rise rapidly initially so that the fitted curve is substantially linear, and will then plateau after about 40–70 minutes, as the process of formation and exhalation of cleavage product or products reaches a steady state. Eventually, as the administered urea is cleaved, the concentration will decrease. The analysis is preferably performed before the curve of measured values reaches a plateau.

This fitting and analysis of a curve of measured concentrations represents a significant improvement over the prior art. Prior art non-radioactively labelled urea breath tests require a significant length of time, such as 30 minutes, to be able to detect the presence of a cleavage product in the exhaled breath of the subject, as described in the Background section above. Such a significant length of time is required because it is inconvenient to obtain more than one sample in these tests, since the sample must be collected and then sent to another laboratory for analysis. Furthermore, if radioactive isotopes, such as carbon-14, are used, the test cannot be performed in the office of the average physician. In any case, the analysis is done separately, so that another office visit is required in order to discuss the results, potentially decreasing client compliance.

However, the method of the present invention allows repeated breath samples to be rapidly obtained and then maximizes both the speed and the accuracy of analysis by fitting the measured values to a curve and then calculating the rate of increase of the curve, which is the derivative.

Specifically, the method of analysis involves the following steps. A plurality of samples of exhaled breath of the subject is collected rapidly, on the order of one sample about every few seconds, preferably such that at least a majority, and most preferably substantially all of the exhaled breaths of the subject are sampled. Next, the concentration of a cleavage product is measured. A curve is fitted to these measured concentrations. The rate of rise of the curve is calculated by derivation, preferably after the measurement of the concentration of a cleavage product in each sample. This analysis of the curve indicates the level of Helicobacter pylori activity in the gastrointestinal tract of the subject. A rapid rise in the measured concentrations, would indicate a high level of activity in the subject.

The calculation of the derivative has a number of advantages over other methods of analysis, such as the calculation of the integral. First, the calculation of the derivative does not require a reference breath sample to be obtained before urea is administered to the subject. Since the derivative represents the rate of increase of the measured concentrations of a cleavage product or products, the starting concentration of that cleavage product or products is unimportant. However, the initial concentration of the cleavage product or products in the reference breath sample is important for the proper calculation of the integral, since such an initial concentration represents a background value which must be substracted from the measured concentrations after administration of the urea.

After the resultant measurement has reached a predetermined level of accuracy, or after a predetermined time period has elapsed, no more samples are collected.

Such a method has a number of advantages. First, the exhaled breath of the subject can be analyzed in real time; that is, there is relatively little delay between the time the Helicobacter pylori activity takes place, and the time such activity is measured. Second, the samples of exhaled breath are obtained rapidly and are analyzed immediately in a manner which substantially increases the accuracy of the results. Third, since multiple samples are obtained, the accuracy of the test is increased. Fourth, there is less statistical error since many samples are collected. Fifth, since samples are preferably collected until a preset level of accuracy is reached, ambiguous results can be substantially eliminated, preventing the need for repeating the test. Thus, such a breath test clearly has a number of advantages over previously known urea breath tests.

EXAMPLE 1

Methods of Fitting the Measured Data to a Curve

Many methods of fitting the measured data to a curve are well known in the art and are presented, for example, in Chapter 15 of Numerical Recipes in C, herein incorporated by reference purely to illustrate examples of the methods for fitting data.

As noted above, the measured data points art- likely to have a characteristic behavior. Initially, the concentration of the cleavage product or products will rise rapidly, as the administered urea is cleaved by urease. However, as the administered urea is either cleaved, absorbed or otherwise removed, the concentration of the cleavage product or products will first reach a plateau, and finally will start to decrease. Since, as noted above, preferably the breath test of the present invention is performed relatively rapidly, preferably the measurements are made when the concentration of the cleavage product or products is rising in a substantially straight line.

Methods for fitting data to a substantially straight line include linear regression, for example. Examples of methods of performing linear regression are given in Numerical Recipes in C, p. 661–666. Of course, other such prior art methods could be used.

Another example of a method which could be used is fitting by linear least squares. Examples of how to perform this method are given in Numerical Recipes in C, p. 671–681. Of course, other such prior art methods could be used.

These examples are intended for illustration only, as methods by which the measurements obtained can be fitted to a substantially linear curve.

EXAMPLE 2

Methods of Calculating the Derivative

A number of prior art methods are available for the calculation of a derivative, as described in Numerical Recipes in C, Chapter 5. Derivatives can be calculated numerically, for example, as described on p. 186–189.

EXAMPLE 3

A Method for Performing the Breath Test and Analysis

This method is intended as an illustrative example only of the breath test of the present invention and is not meant to be limiting.

First, carbon-13 isotopically-labelled urea is administered to a subject. Next, after about eight minutes, the subject exhales into a nasal cannula, which is connected to the measuring instrument, about once every ten seconds. The measuring instrument determines the concentration of carbon-13 isotopically-labelled carbon dioxide in each breath of the subject. The instrument then fits the concentrations to a curve by using linear regression. Next, the derivative is calculated by a numerical method. The fitting of the curve and the calculation of the derivative is repeated for three minutes or about twenty breaths, at which point the subject stops exhaling into the nasal cannula and the test is finished.

While the invention has been described with respect to a limited number of embodiments, it will be appreciated that many variations, modifications and other applications of the invention may be made.

What is claimed is:

1. A method for the diagnosis of *Helicobacter Pylori* in the gastrointestinal tract of a subject, comprising the steps of:
   (a) administering isotope-labeled urea to the subject, said isotope-labeled urea being cleavable by urease to form a cleavage product;
   (b) having said subject exhale repeatedly into analyzing equipment;
   (c) analyzing a plurality of exhaled breaths of the subject substantially in real time while the subject's exhalation contains the cleavage product, if present, to determine a plurality of concentrations of said cleavage product; and
   (d) analyzing said plurality of concentrations to indicate *Helicobacter Pylori* activity in the gastrointestinal tract of said subject, wherein the step of analyzing said exhaled breath of the subject is repeated substantially continuously until a predetermined accuracy for analyzing said plurality of concentrations is reached.

2. The method of claim 1, wherein the step of analyzing said exhaled breath of the subject is repeated substantially continuously until a predetermined time period has elapsed.

3. The method of claim 1, wherein said exhaled breath of the subject is analyzed by an infrared spectrometer.

4. The method of claim 1, wherein said cleavage product is carbon dioxide.

5. The method of claim; wherein said carbon dioxide is carbon-13 isotopically-labelled.

6. The method of claim 1, wherein said cleavage product is ammonia.

7. The method of claim 6, wherein said ammonia is nitrogen-15 isotopically-labelled.

8. The method of claim 1, wherein the step of using said plurality of concentrations is performed by fitting said concentrations to a curve.

9. The method of claim 8, wherein said curve is analyzed by inspecting its derivative.

10. The method of claim 2, and wherein said particular time period is such that said concentrations are still increasing before said predetermined time period has elapsed.

* * * * *